US006986288B2

(12) United States Patent
Ichikawa et al.

(10) Patent No.: US 6,986,288 B2
(45) Date of Patent: Jan. 17, 2006

(54) METHOD FOR EVALUATING A WELDED PART (75) Inventors: Hiroshi Ichikawa, Shizuoka-ken (JP); Tadahisa Sakaguchi, Shizuoka-ken (JP); Nobuyuki Asakura, Shizuoka-ken (JP)

(73) Assignee: Yazaki Corporation, Tokyo (JP)

( * ) Notice: Subject to any disclaimer, the term of this patent is extended or adjusted under 35 U.S.C. 154(b) by 25 days.

(21) Appl. No.: 10/756,306

(22) Filed: Jan. 14, 2004

(65) Prior Publication Data
US 2004/0187596 A1    Sep. 30, 2004

(30) Foreign Application Priority Data
Jan. 15, 2003    (JP) .......................... P2003-007324

(51) Int. Cl.
*G01N 3/20*    (2006.01)
(52) U.S. Cl. ........................................ 73/850
(58) Field of Classification Search ............... 73/849, 73/850, 851; 219/109
See application file for complete search history.

(56) References Cited

U.S. PATENT DOCUMENTS

| 5,397,872 A | * | 3/1995 | Baker et al. ................. 219/109 |
| 5,406,044 A | * | 4/1995 | Killian et al. ................. 219/99 |
| 5,587,537 A | * | 12/1996 | Simmons ................ 73/862.392 |
| 5,973,287 A | * | 10/1999 | Takano ......................... 219/56 |
| 5,977,508 A | * | 11/1999 | Takano ......................... 219/109 |
| 6,393,924 B1 |   | 5/2002 | Eder et al. ..................... 73/850 |

FOREIGN PATENT DOCUMENTS

JP            07-130293        5/1995

* cited by examiner

*Primary Examiner*—Max Noori
(74) *Attorney, Agent, or Firm*—Finnegan, Henderson, Farabow, Garrett & Dunner, L.L.P.

(57) ABSTRACT

In the method for evaluating a welded part, it is performed to make an inspection press member press the welded part for connecting a plurality of wires with each other to apply a predetermined compressive load on the welded part. Next, it is performed to measure an amount of strain of the welded part when it is subjected to the compressive load. The evaluation of the welded part in welding condition is carried out by judging whether or not the measured amount of strain is within a predetermined range.

8 Claims, 13 Drawing Sheets

FIG.11
BREAKING TEST OF WELDED PART

METHOD FOR EVALUATING A WELDED PART

BACKGROUND OF THE INVENTION

The present invention relates to a method for evaluating a welded part on production. More particularly, the present invention relates to a method for evaluating whether the welded part has a strength more than a desired strength.

In a manufacturing process for electrical products, for example, there is a process of electrically connecting conductive members with each other through a welded part. Here, the producing order of such a welded part is described by one example of electrical wires as the conductive members, in brief.

Figure 1A:
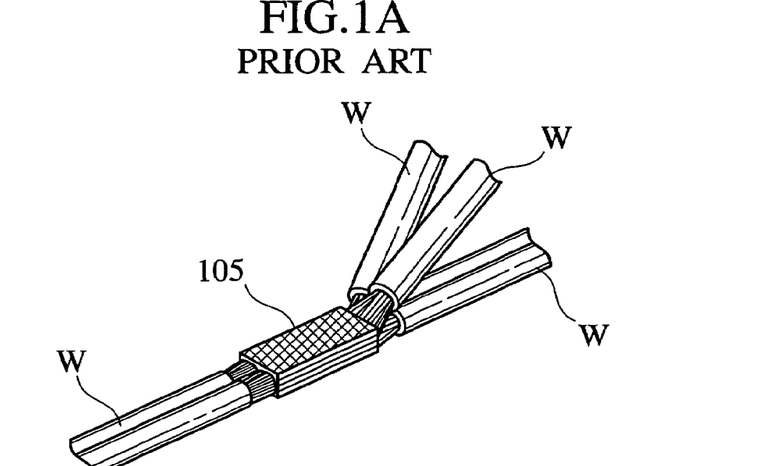
FIGS. 1A, 1B and 1C are perspective views of various welding forms, each showing welded parts of wires by ultrasonic welding.
Figure 1B:
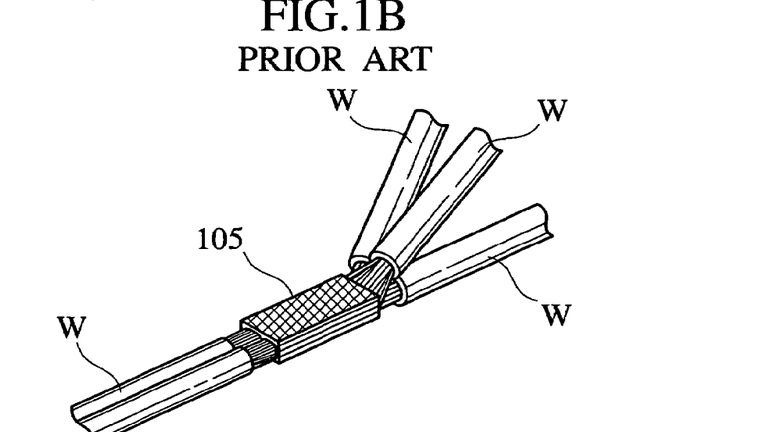
Figure 1C:
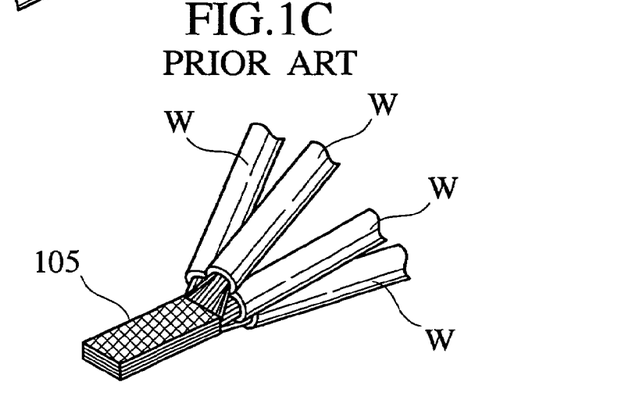

For instance, it is carried out to arrange respective cores of plural wires between an ultrasonic horn and an anvil and further carried out to apply a compression and ultrasonic vibrations on the cores of the wires pinched between the ultrasonic horn and the anvil. Then, the resulting ultrasonic energy allows the cores to be molten thereby producing a welded part among the cores. FIGS. 1A, 1B and 1C shows various welded forms each obtained by connecting a plurality of wires W with each other through a welded part (or welded part) 105 in accordance with the above-mentioned welding order. As for the welded part 105 by ultrasonic welding etc., it is subsequently carried out to inspect whether the welded part 105 is in an appropriate welded condition or not in order to prevent shipment of defective products.

Figure 2A:
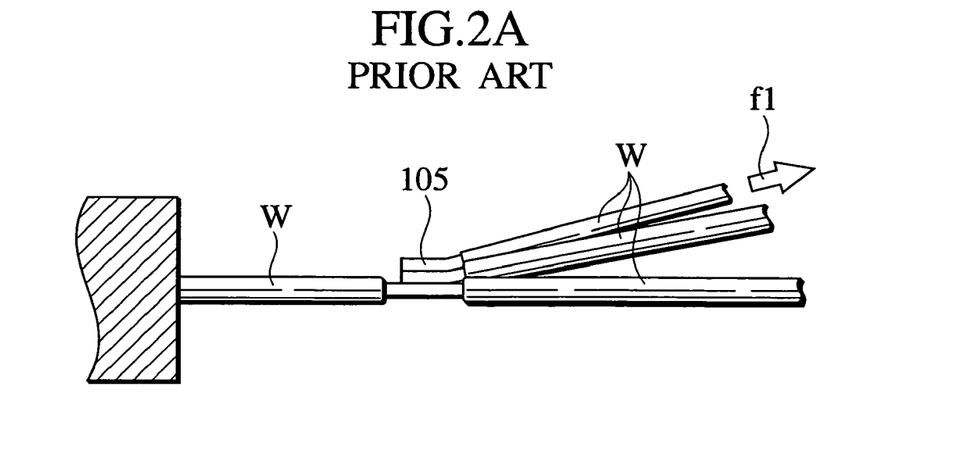
FIGS. 2A, 2B and 2C are perspective views each showing tensile tests of the welded part of the wires in various welding forms.
Figure 2B:
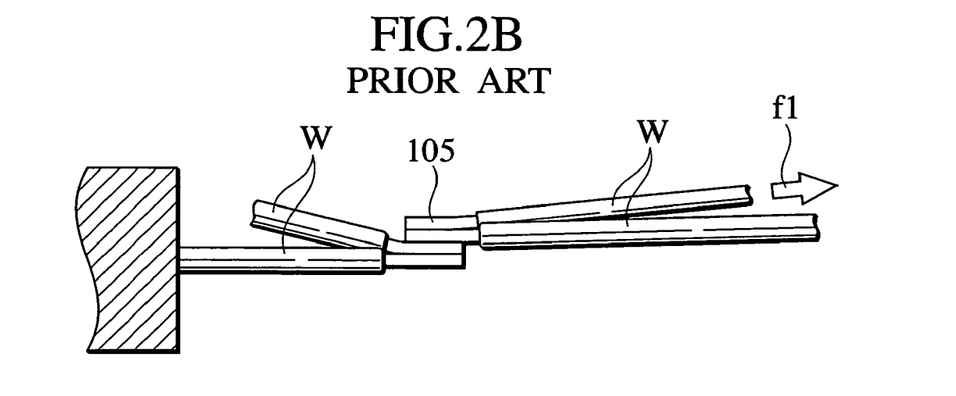
Figure 2C:
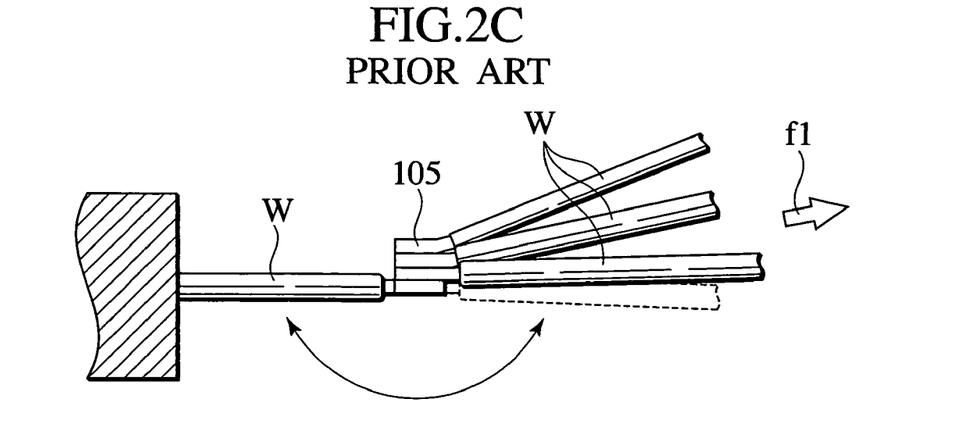

FIGS. 2A, 2B and 2C show one conventional method for evaluating such a welded part. According to the conventional evaluation method, on condition of fixing one wire W, a predetermined tensile force f1 is applied on the other wire W. Thus, by acting the tensile force f1 on the welded part 105, it is estimated whether the welded condition is proper or not. In detail, if the welded part 105 is not broken in spite of the application of the tensile force f1, then it is judged that the welded part 105 is nondefective. While, if the structure 105 is broken, it is judged that the structure 105 is defective.

Figure 3:
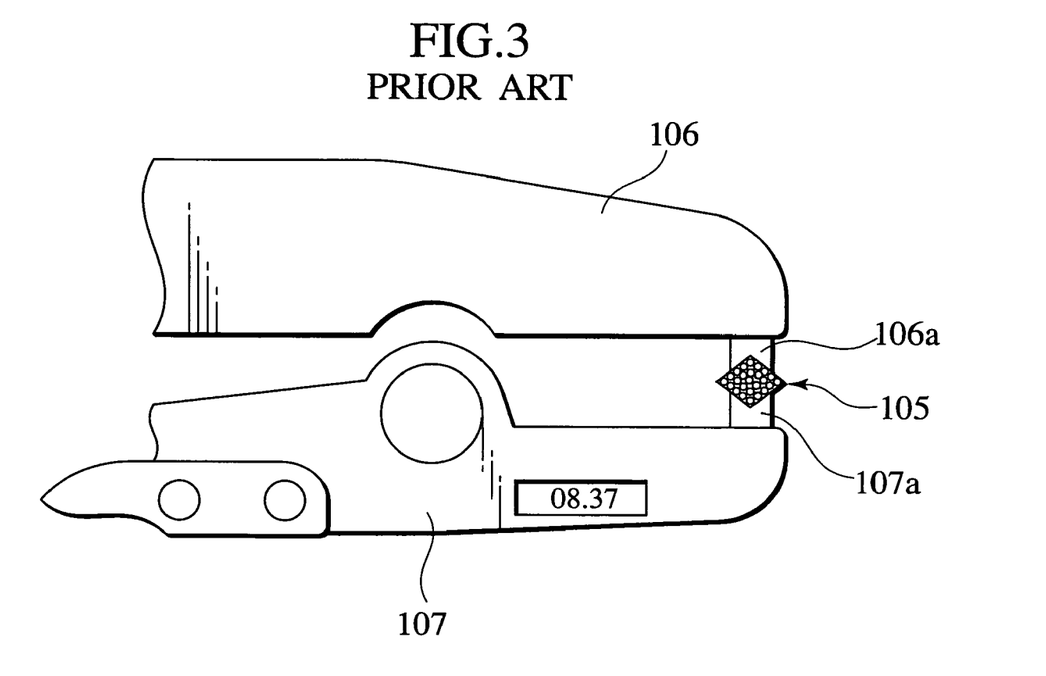
FIG. 3 is a perspective view showing the conventional compression test of a welded part of wires.
Figure 4:
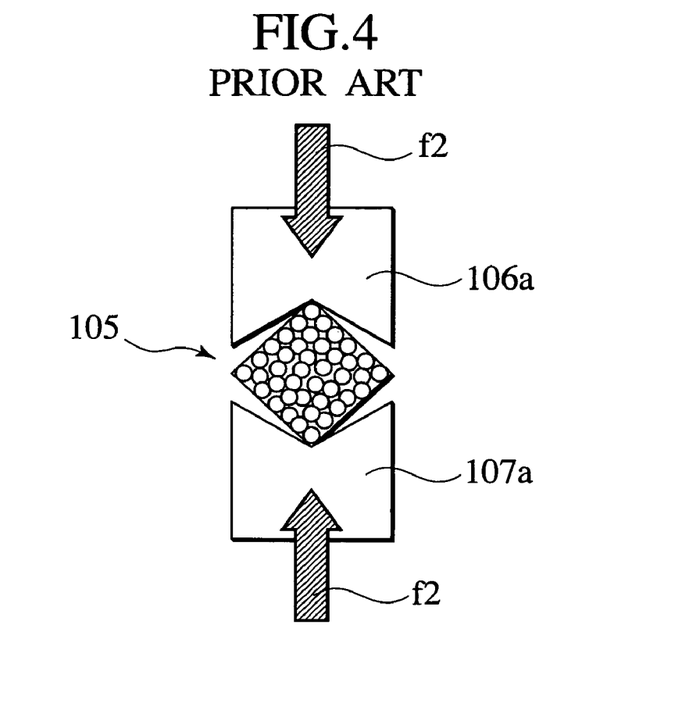
FIG. 4 is a front view showing, in prior art, the welded part of the wires under the compression test when the welded part is nondefective.
Figure 5:
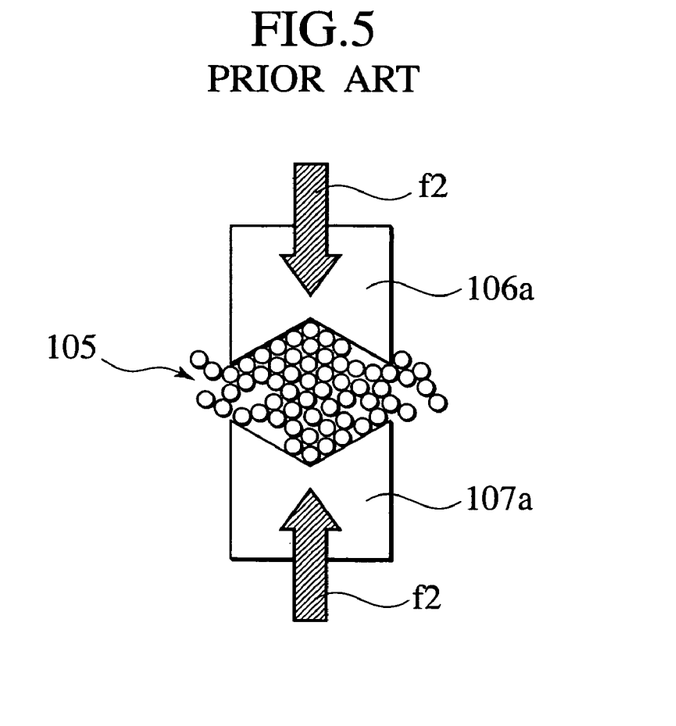
FIG. 5 is a front view showing, in prior art, the welded part of the wires under the compression test when the welded part is defective.

As the other conventional evaluation method for such a welded part, FIGS. 3, 4 and 5 show one evaluation method disclosed in U.S. Pat. Publication No. 6,393,924. According to this evaluation method, as shown in FIG. 3, a welded part 105 is pinched between holding parts 106a, 107a of a pair of arm members 106, 107. In this state, a compressive force f2 is applied on the welded part 105 in order to judge whether such a welded condition is proper or not. In detail, on the application of the compressive force f2 on the welded part 105, it is judged that a product with the structure is 105 is nondefective unless it is broken as shown in FIG. 4. While, if the welded part 105 is broken as shown in FIG. 5, then it is judged that the product is defective.

In the conventional evaluation methods mentioned above, however, it is noted that the welded part 105 is subjected to such a tensile or compressive force that the part 105 might be broken. That is, a product on completion of the above inspection is not worthy of being a good product even if the welded part is not broken. Therefore, since the above evaluation methods require some evaluation samples to be picked up from a flow of products, an amount of production is influenced due to the presence of evaluation samples.

SUMMARY OF THE INVENTION

Under such a situation, it is therefore an object of the present invention to provide a method for evaluating a welded part, which does not incur waste due to evaluation inspection, with high reliability.

The above-mentioned object can be solved by providing a method for evaluating a welded part, comprising: applying a predetermined compressive load for inspection on the welded part; measuring an amount of strain (strain value) of the welded part when the compressive load is applied thereon; and evaluating the welding condition of the welded part by judging whether or not the amount of strain on measurement is included in a predetermined range.

Generally, in a defective welded part having its welding condition of low strength, welded elements (e.g. wire cores) forming the welded part are arranged roughly, so that the welded part reaches a yield point by a small compressive load. While, in a nondefective welded part having its welding condition of high strength, welded elements forming the welded part are arranged closely, so that the welded part reaches a yield point by a large compressive load. Corresponding to such a difference in compressive load causing a yield between the defective welded part and the nondefective welded part, there is a great difference in strain value corresponding to the compressive load about the yield point therebetween. Therefore, while making use of such a characteristic difference between the defective welded part and the nondefective welded part, if the inspection is carried out at a compressive load such that the defective welded part of low strength would be deformed while exceeding its yield point and the nondefective welded part of high strength would be elastically deformed without exceeding its yield point, then it becomes possible to estimate the welding condition of one welded part by detecting its amount of strain under the compressive load. Further, since this compressive load for the inspection is so small as to allow the welded elements of the nondefective welded part to be deformed elastically, all of the articles equipped with the nondefective welded parts after the inspection can be used as formal products, whereby it is possible to inspect all of manufactured articles in welding evaluation.

In a preferred embodiment of the invention, the compressive load may be applied on a part of the surface of the welded part.

In this case, since there is remained an inspection trace on the surface of the welded part after the inspection, it is possible for an inspection staff to visibly confirm whether the corresponding article has been inspected or not. Additionally, since this evaluation method allows a compressive load at the inspection to be reduced, it is possible to miniaturize and simplify an inspecting apparatus embodying the method. Since the compressive load at the inspection is applied to only part of the welded part, it is possible to reduce the damage on the welded part at the inspection.

On the assumption of applying the predetermined compressive load for inspection on the welded part, the above method for evaluating the welded part further may comprise:

sampling information about yield loads corresponding to welding degrees of a plurality of welded parts in their welding conditions; making a correspondence data consisting of the welding degrees and the corresponding yield loads; and searching a relationship between the welding degrees and the yield loads, wherein the compressive load for inspection is determined on the ground of the searched relationship.

Then, since the compressive load at the inspection is a value of high reliability based on the correspondence data, it is possible to exclude a welded part of low strength in welding condition certainly.

In the preferred embodiment, there are established, as the welding degrees of the welded parts, a low-strength zone where welded elements forming the welded part are arranged roughly, a high-strength zone where welded elements forming the welded part are arranged closely and a normal-strength zone where welded elements forming the welded part are arranged with an intermediate density between the low-strength zone and the high-strength zone, and the compressive load for inspection is determined within a range of yield loads of the welded parts included in the normal-strength zone.

In this case, owing to the establishment of one buffer area named "normal-strength zone", the reliability of inspection is so improved that it is possible to exclude manufactured articles having low strength in welding condition certainly.

In the above evaluation method, the welded part has a plurality of wires welded with each other.

In this case, it is possible to obtain the above-mentioned effects for the welded part of a plurality of wires.

In the above evaluation method, the welded part may be formed by means of ultrasonic welding.

Also in this case, it is possible to obtain the above-mentioned effects for the welded part formed by means of ultrasonic welding.

In the above evaluation method, the compressive load may be applied on the welded part through an inspection press member that is adapted so as to press the surface of the welded part.

In this case, it is possible for an inspection staff to confirm an inspection trace remained on the surface of the welded part after the inspection visually and easily.

In the above evaluation method, the inspection press member may be provided with a wedge-shaped tip.

In this case, owing to the wedge-shaped tip of the inspection press member, it is possible for an inspection staff to confirm an inspection trace remained on the surface of the welded part after the inspection visually and easily.

In the above evaluation method, the inspection press member may be provided with a rounded tip.

Also in this case, owing to the rounded tip of the inspection press member, it is possible for an inspection staff to confirm an inspection trace remained on the surface of the welded part after the inspection visually and easily.

These and other objects and features of the present invention will become more fully apparent from the following description and appended claims taken in conjunction with the accompanying drawings.

BRIEF DESCRIPTION OF THE DRAWINGS

FIGS. 7A, 7B and 7C are sectional diagrams taken along line 7—7 of FIG. 6, in which

FIGS. 12A and 12B show the embodiment of the present invention, in which

DESCRIPTION OF THE PREFERRED EMBODIMENT

An embodiment of the present invention will be described with reference to drawings.

Figure 6:
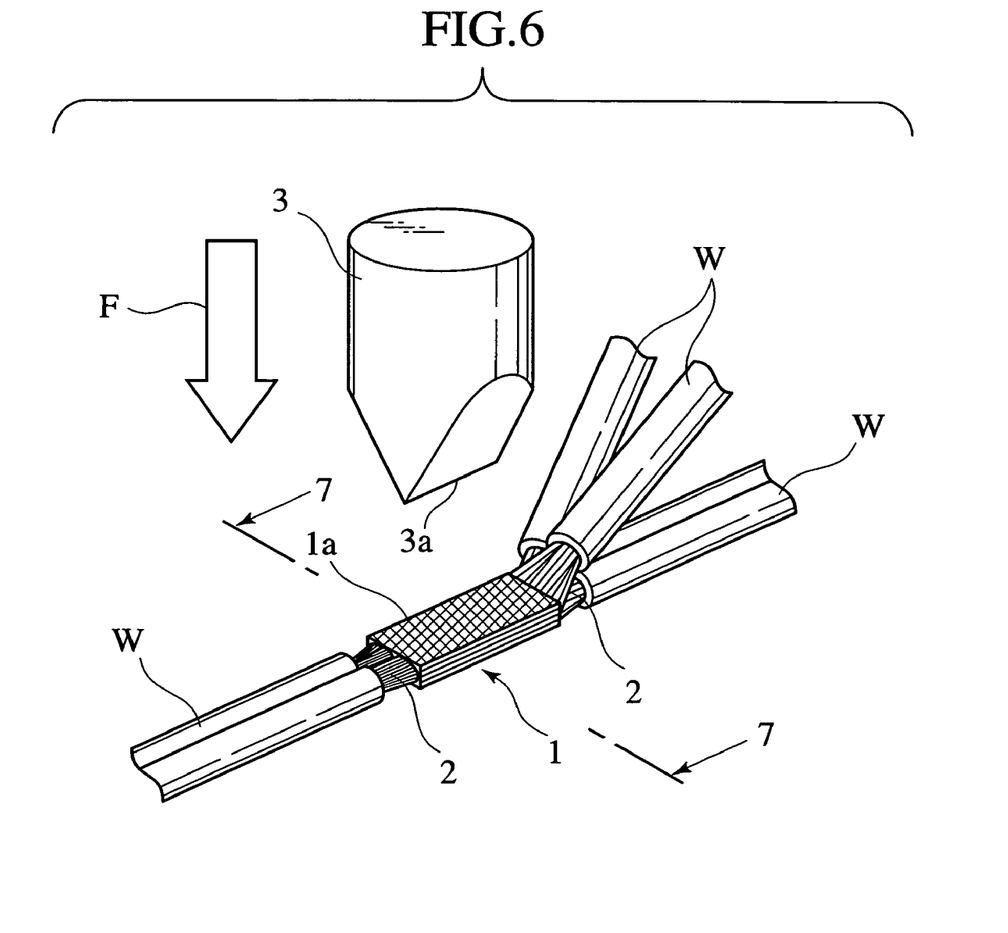
FIG. 6 is a perspective view showing the inspection of the welded part of wires in accordance with one embodiment of the present invention.

As shown in FIG. 6, a plurality of wires W are connected with each other through the intermediary of a welded part (structure) 1. This welded part 1 is completed by melting core lines 2 of the plural wires W by means of ultrasonic energy. In ultrasonic welding to form the welded part 2, the core lines 2 of the wires W are held between an ultrasonic horn and an anvil both of which are not shown in the figure and subsequently, the core lines 2 are subjected to ultrasonic vibrations. As a result, the core lines 2 are molten by ultrasonic energy, providing the welded part 1.

Next, the evaluation method of the welded part 1 will be described below. In accordance with the evaluation method, there are employed an inspection press member 3 for pressing a surface 1*a* of the welded part 1 to apply a compressive load F thereon, compressive-load control means (not shown) for controlling a pressure (compressive load) F of the member 3 and strain measuring means (also not shown) for detecting an amount of strain of the welded part 1 to which a compressive force is applied by the inspection press member 3. In estimation, it is carried out to apply a predetermined compressive load to the welded part 1 by pressing the surface 1*a* through the inspection press member 3. Then, by judging whether an amount of strain of the welded part 1 is within a designated range or not, the welding condition about the welded part 1 is estimated.

The reason why the detection of strain in applying the compressive load to the welded part 1 allows the welding condition to be evaluated is as follows.

Figure 7A:
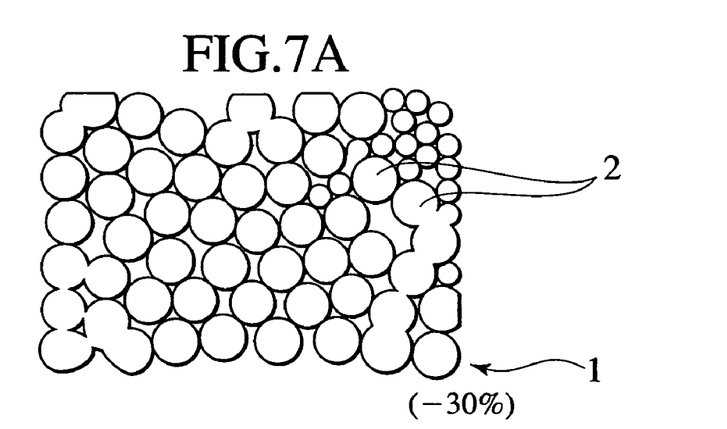
FIG. 7A is a sectional diagram of the welded part having a low strength (−30%) in welded condition.
Figure 7B:
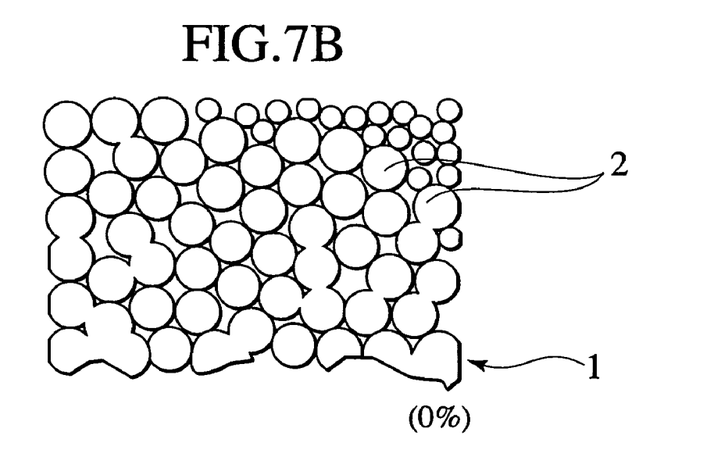
FIG. 7B is a sectional diagram of the welded part having a normal strength (0%) in welded condition and FIG. 7C is a sectional diagram of the welded part having a high strength (+50%) in welded condition.
Figure 7C:
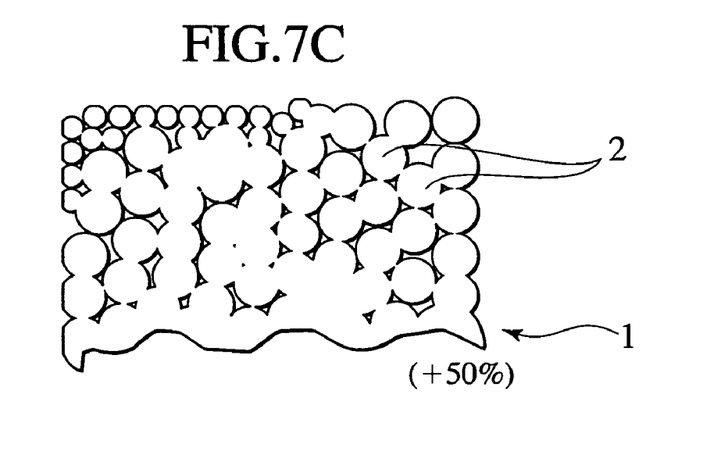

Here, it should be noted that the strength of the welded part 1 depends on the welding condition. As shown in FIG. 7A, when the welded part 1 has a low strength (−30%) in welding condition, the core lines 2 as members to be welded are arranged roughly. Conversely, as shown in FIG. 7C, when the welded part 1 has a high strength (+50%) in welding condition, the core lines 2 are arranged closely. As shown in FIG. 7B, when the welded part 1 has a normal strength (0%) in welding condition, the core lines 2 are arranged with an intermediate density between that of FIG. 7A and that of FIG. 7C.

The meaning of the above percentage representing various welding conditions will be described below.

Figure 8:
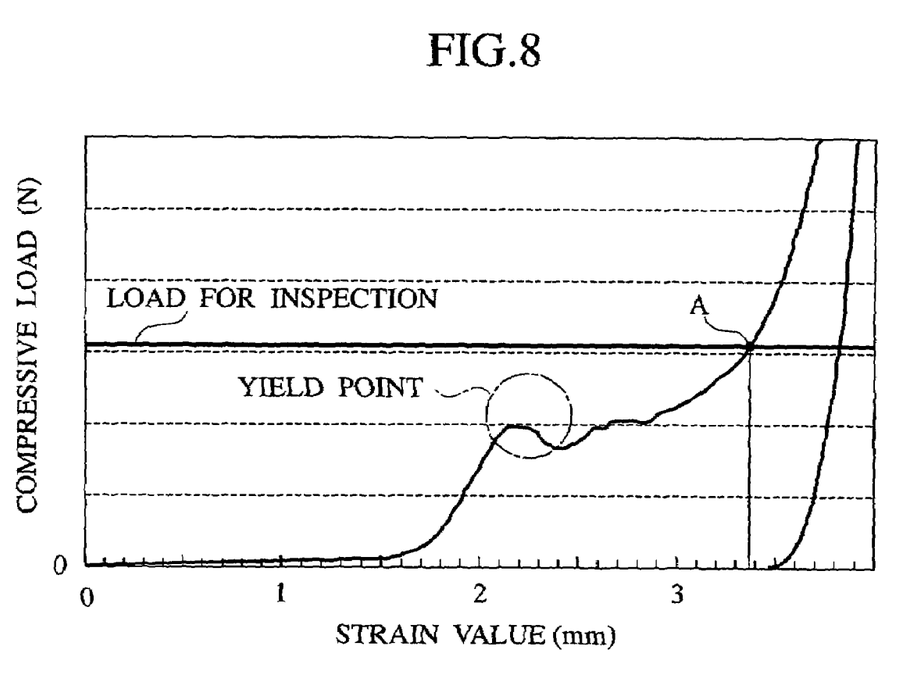
FIG. 8 is a characteristic diagram of the welded part of a low strength in welded condition in accordance with one embodiment of the present invention, showing the relationship between compressive load thereon and strain.
Figure 9:
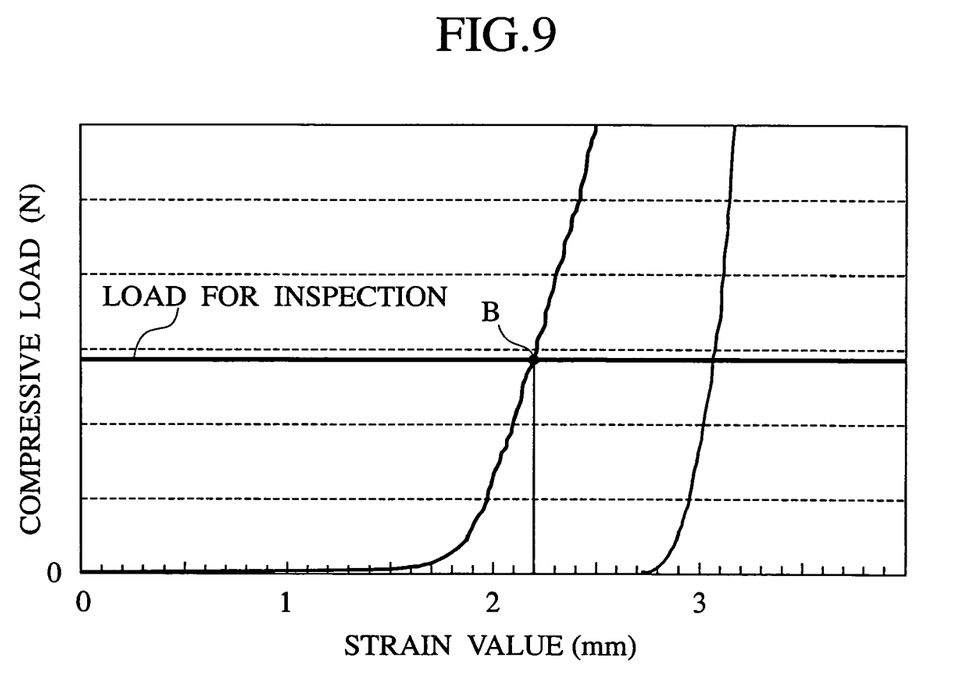
FIG. 9 is a characteristic diagram of the welded part of a high strength in welded condition in accordance with one embodiment of the present invention, showing the relationship between compressive load in its lower range thereon and strain.
Figure 10:
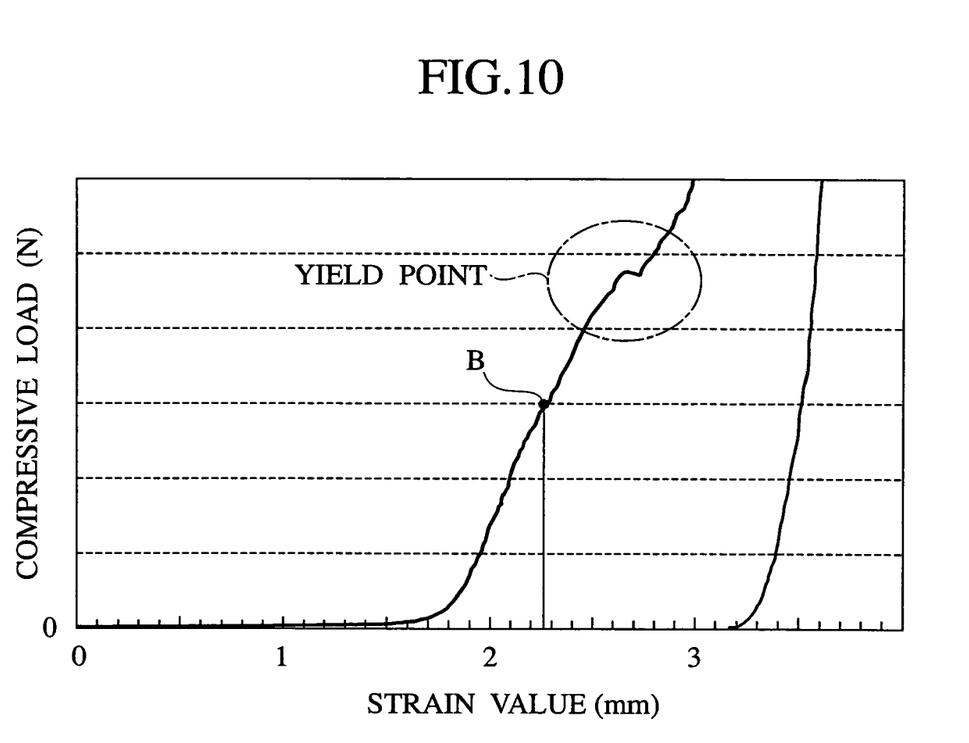
FIG. 10 is a characteristic diagram of the welded part of a high strength in welded condition in accordance with one embodiment of the present invention, showing the relationship between compressive load within its wider range including a yield point and strain.

When the welded part 1 is provided with a low strength, the relationship between compressive load and strain (amount of strain) is established with a characteristic curve shown in FIG. 8. That is, the welded part 1 has a yield point at a small compressive load F. While, when the welded part 1 is provided with a high strength, the relationship between compressive load and strain is established with characteristic curves shown in FIGS. 9 and 10. That is, the welded part 1 has a yield point at a high compressive load F. Additionally, when the welded part 1 is provided with a normal strength, there is established a characteristic curve in the relationship between compressive load and strain, as being middle between the above characteristic curves at low and high strengths, so that the welded part 1 has a yield point at an intermediate compression load F. As shown in FIGS. 8 and 10, with an increase in the compressive load F, the amount of strain changes greatly since its yield point as a boundary. Now, it is assumed that the compressive load F at inspection is set to 1500 N, for example. In such a situation, if the welded part 1 has a low strength (−30%) in welding condition, the same part 1 will be deformed with a large strain, for example, about 3.4 mm (see a point A of FIG. 8) while exceeding the yield point. While, in the above situation, if the welded part 1 has a high strength (+50%) in welding condition, the same part 1 will be elastically deformed with a small strain, for example, about 2.2 mm (see a point B of FIG. 9) without exceeding the yield point. That is, under the same evaluation situation, there is a great difference in strain between the welded part 1 of low strength and that of high strength.

This means that if the inspection is carried out at a compressive load such that the welded part 1 of low strength would be deformed while exceeding the yield point and the welded part 1 of high strength would be elastically deformed without exceeding the yield point, then detecting of the amount of strain allows the welded part 1 to be valuated in terms of its welding condition.

The above compressive load F at inspection and the strain value for judgment will be determined as follows.

Figure 11:
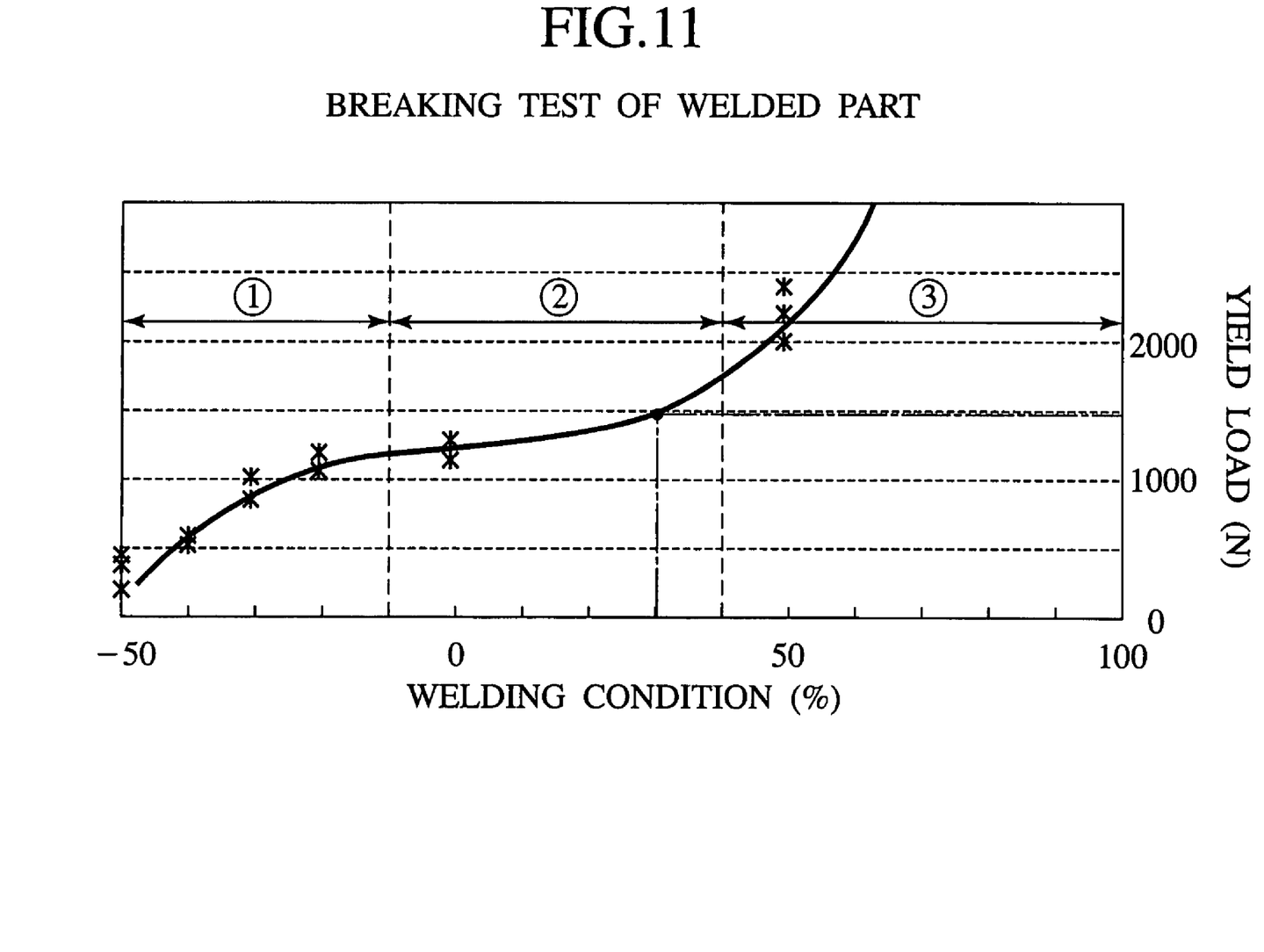
FIG. 11 is a characteristic diagram of the relationship between welding evaluation of the welded part (welding condition) and breaking load, showing one embodiment of the present invention.

Under a situation that the welding condition is controlled sufficiently, it is firstly performed to produce various welded parts 1 of different welding conditions (−50%~+100%) by changing one or more welding conditions, such as welding pressure. Next, corresponding to the above evaluation degree, it is performed to measure respective yield points of the welded parts 1 and further plot sampling data of yield points on a diagram as shown in FIG. 11. In FIG. 11, various points with marks X denote sampling points. Next, as shown in FIG. 11, it is performed to make a characteristic curve about the relationship between the degree of evaluation for the welding condition (welding degree) and the yield load. Additionally, as shown in FIG. 11, the evaluation range for the welding condition is divided into: ① low-strength zone (−50%~−10%) producing defective products; ② normal-strength zone (−10%~+40%); and ③ high-strength zone (+40%~+100%) producing nondefective products. Then, the breaking strength in the normal-strength zone ② is established as the compressive load at inspection. For example, since the breaking strength in the normal-strength zone ② ranges from approx. 1250 N to approx. 1750 N in FIG. 11, a compressive load within this range is established as the compressive load F (e.g. 1500 N) for inspecting the welding degree. Simultaneously, it is carried out to select an appropriate value (e.g. 2.5 mm) within the range of strain corresponding to the normal-strength zone ② and further set the so-selected value as the strain value for judgment.

By establishing the so-determined compressive load as the compressive load F (e.g. 1500 N) at inspection, respective strain values of the welded parts 1 on production are measured. Again noted that if the welded part 1 is provided with a low strength, then it is deformed while exceeding the yield point and that if the welded part 1 is provided with a high strength, then it is deformed without exceeding the yield point, thereby producing a great difference in strain between the former welded part 1 and the latter welded part 1. In detail, when the welding strength of the welded part 1 is low (−30%), the strain value amounts to e.g. approx. 3.4 mm (point A) in FIG. 8. While, when the welding strength of the welded part 1 is high (+50%), the strain value amounts to e.g. approx. 2.2 mm (point B) in FIG. 9. Thus, since the welded part 1 of low strength is deformed with a strain value more than 2.5 mm, it is judged that a product with such a welded part 1 is defective. While, since the welded part 1 of high strength is deformed with a strain value less than 2.5 mm, it is judged that a product with such a welded part 1 is nondefective. According to the invention, since a compressive load F for the inspection is so small as to allow the core lines 2 of the nondefective welded part 1 (high strength) to be deformed elastically, the nondefective samples after the inspection can be used as formal products. Therefore, it is possible to accomplish the total inspection of manufactured articles while abolishing the sampling inspection, whereby the nondefective articles after the inspection can be shipped as finished products. In this way, according to the present invention, it is possible to attain the inspection with high reliability without incurring waste due to the inspection.

In the above-mentioned embodiment, there are performed steps of: sampling a variety of yield loads corresponding to the evaluation degrees of the welded parts 1 in terms of their welding conditions; making a correspondence data consisting of various evaluations in welding condition and breaking loads of the samples; and establishing a compressive load for inspection on the ground of the correspondence data. Thus, since the compressive load F for inspection is established with high reliability based on the correspondence data, it is possible to exclude manufactured articles having low strength in welding condition certainly.

In the above-mentioned embodiment, additionally, the normal-strength zone in the evaluation of welding condition is established between the low-strength zone and the high-strength zone and further, the compressive load F is selected from breaking loads within the normal-strength zone. Thus, owing to the establishment of one buffer area named "normal-strength zone", the reliability of inspection is so improved that it is possible to exclude manufactured articles having low strength in welding condition certainly.

Next, the relationship between the area of the tip surface 3a of the inspection press member 3 and the surface area of the welded part 1 will be described below. The tip surface 3a of the inspection press member 3 is formed with an area S narrower than the surface area of the welded part 1. In the shown embodiment, the tip surface 3a is smaller than the surface 1a of the welded part 1 lengthwise and crosswise, about one-fourth of the surface 1a.

Figure 12A:
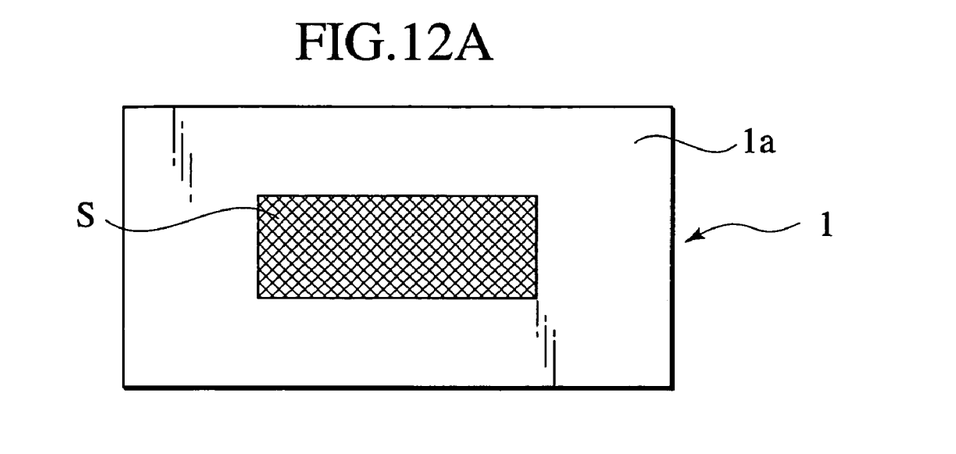
FIG. 12A is a plan view showing a press area (cross-hatching) of the welded part and FIG. 12B is a perspective view of the welded part after inspection.
Figure 12B:
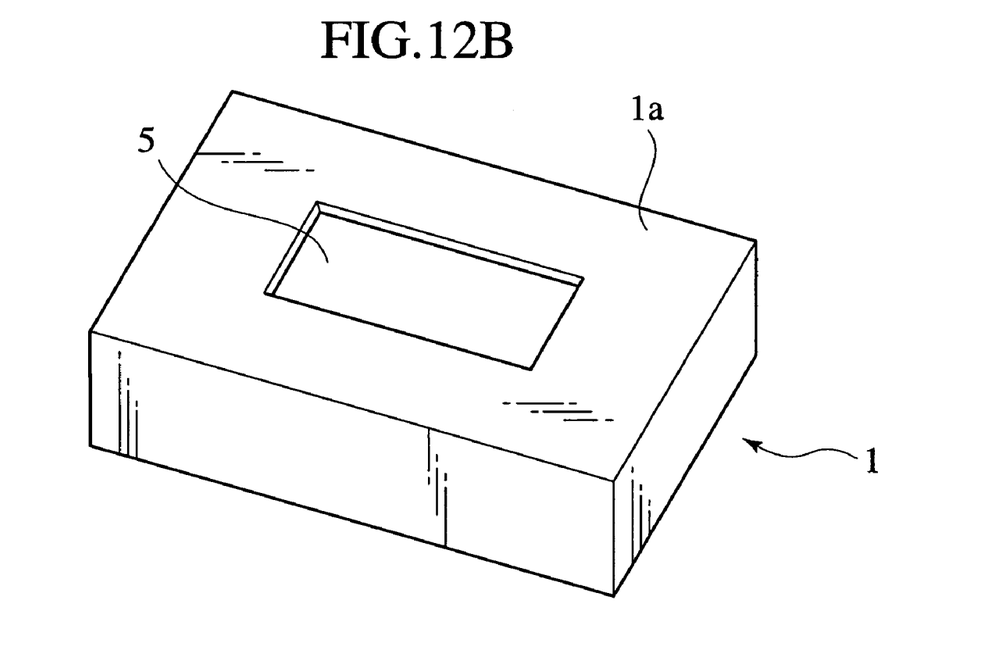

On completion of the inspection to make the tip surface 3a of the inspection press member 3 press the surface 1a of the welded part 1 through the press area S (FIG. 12A), there is remained an inspection trace 5 on the surface 1a of the welded part 1, as shown in FIG. 12B. Since the inspection trace 5 enables an inspection staff (not shown) to confirm whether an article has been inspected or not, it is possible to prevent an occurrence of leakage in the inspection.

Additionally, since the evaluation method of the invention allows a compressive load at the inspection to be reduced, it is possible to miniaturize and simplify an inspecting apparatus embodying the method.

Since the compressive load at the inspection is applied to only part of the welded part 1, it is possible to reduce the damage on the welded part 1 at the inspection.

Figure 13:
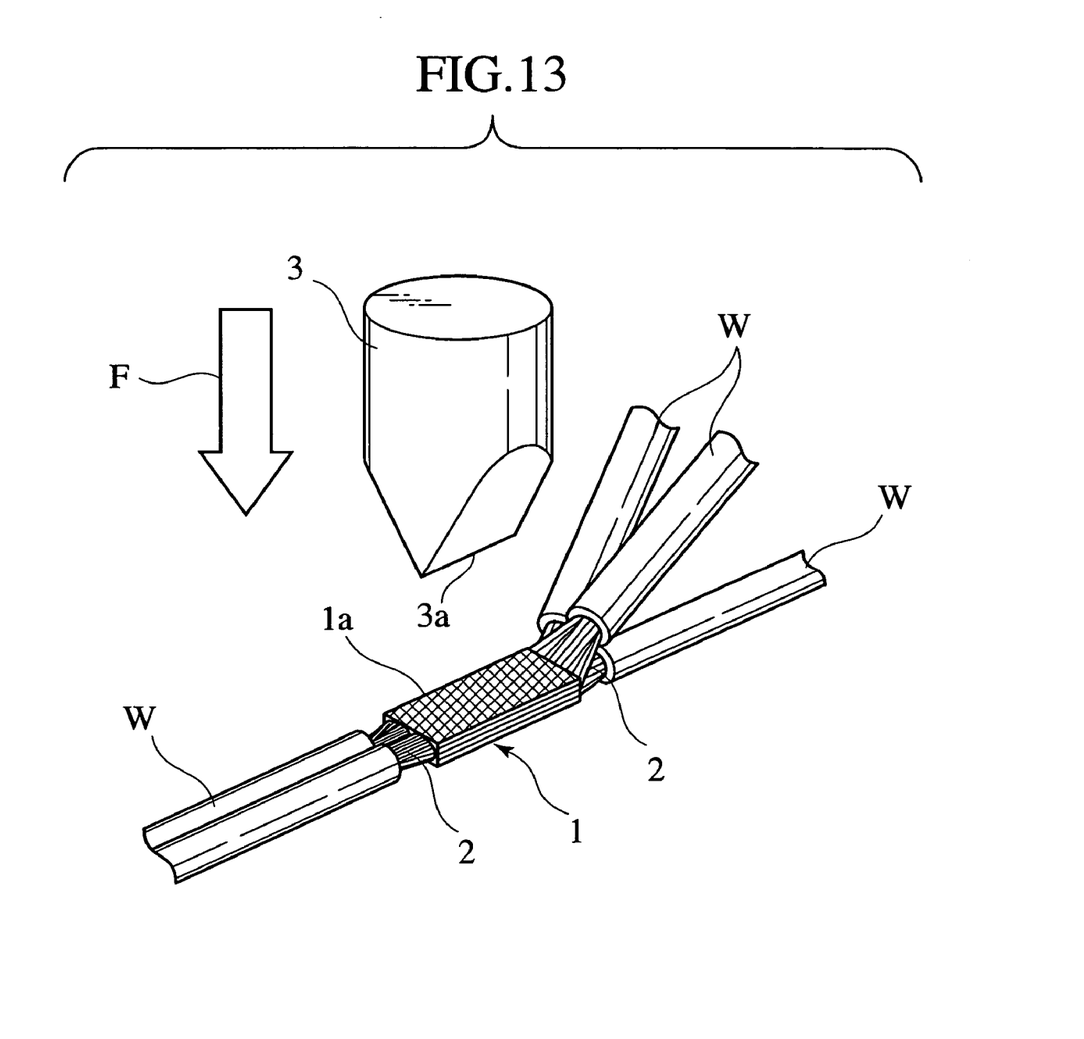
FIG. 13 is a perspective view showing the inspection of the welded part of wires, in a different welding form.
Figure 14:
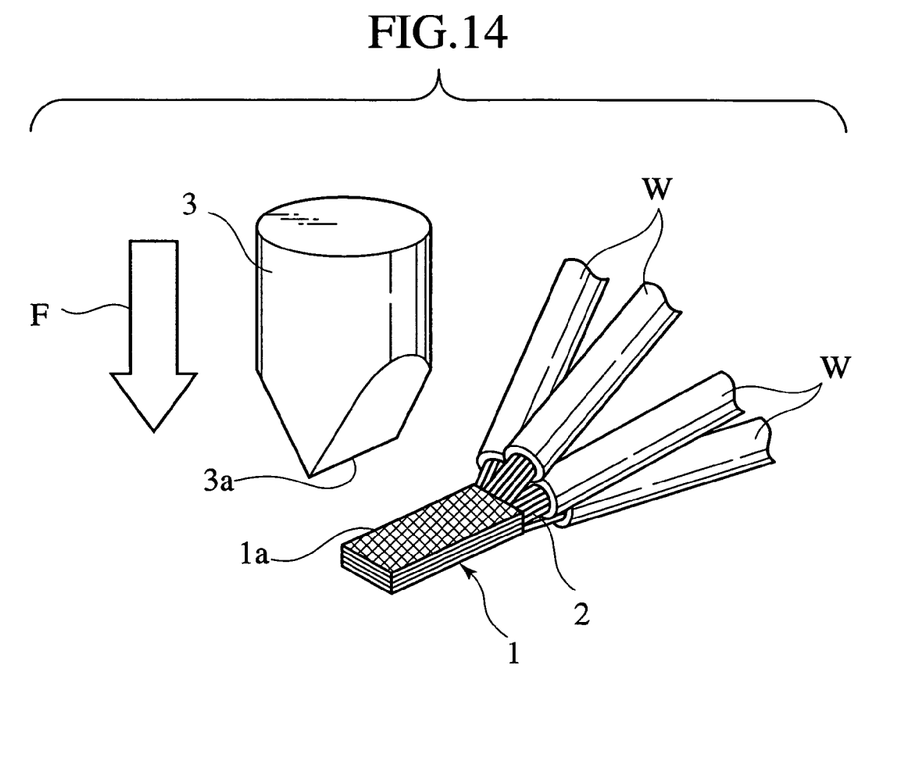
FIG. 14 is a perspective view showing the inspection of the welded part of wires, in a different welding form.

FIGS. 13 and 14 are perspective views each showing the inspection of the welded parts 1 for the wires W in different welding forms. As shown in FIGS. 13 and 14, it is a matter of course that these welded parts 1 can be inspected in evaluation in the same way as above.

Noted that, as shown in FIGS. 6, 13 and 14 each, although the tip surface 3a of the inspection press member 3 is formed to be flat, the same surface may be rounded in the modification. Although the tip of the inspection press member 3 is wedge-shaped, it may be formed to be a circular cone or a pyramid.

Although the evaluation of the welded part 1 in welding condition is classified within the range of −50% to +100% in the above-mentioned embodiment, the evaluation method of the invention may employ the other classification.

Although the evaluation range for the welding condition is divided into: ① low-strength zone (−50%~−10%) producing defective products; ② normal-strength zone (−10%~+40%); and ③high-strength zone (+40%~+100%) in the above-mentioned embodiment, of course, the classification may be altered in terms of numerical value and range while depending on the required quality of products. Furthermore, regarding the compressive load for inspection and the strain value for judgment, they may be appropriately altered dependently on the required quality of products.

Although a plurality of wires W are connected to each other through the welded part 1 that is estimated in welding condition in the above-mentioned embodiment, the present invention is applicable to the evaluation of a welded part formed between conductive members.

Further, although the evaluation method of the invention is directed to the evaluation of the welded part 1 obtained by ultrasonic welding, of course, the present invention is applicable to the evaluation of a welded part formed by the other hot-welding.

As mentioned above, in a defective welded part having its welding condition of low strength, welded elements forming the welded part are arranged roughly, so that the welded part reaches a yield point by a small compressive load. While, in a nondefective welded part having its welding condition of high strength, welded elements forming the welded part are arranged closely, so that the welded part reaches a yield point by a large compressive load. Corresponding to such a difference in compressive load causing a yield between the defective welded part and the nondefective welded part, there is a great difference in strain value corresponding to the compressive load about the yield point therebetween. Therefore, according to the present invention, while making use of such a characteristic difference between the defective welded part and the nondefective welded part, since the evaluation is carried out at a compressive load such that the defective welded part of low strength would be deformed while exceeding its yield point and the nondefective welded part of high strength would be elastically deformed without exceeding its yield point, it is possible to estimate the welding condition of one welded part by detecting its amount of strain (or strain value) under the compressive load. Further, since this compressive load for the inspection is so small as to allow the welded elements of the nondefective welded part to be deformed elastically, all of the articles equipped with the nondefective welded parts after the inspection can be used as formal products, whereby it is possible to inspect all of manufactured articles in welding evaluation. Thus, the present evaluation method does not incur waste due to inspection, with high reliability.

The scope of the invention is defined with reference to the following claims.

What is claimed is:

1. A method for evaluating a welded part, comprising:
   sampling information about yield loads corresponding to welding degrees of a plurality of welded parts in their welding conditions;
   making a correspondence data including the welding degrees and the corresponding yield loads;
   searching a relationship between the welding degrees and the yield loads and determining a compressive load for inspection on the ground of the searched relationship;
   applying the determined compressive load for inspection on the welded part;
   measuring an amount of strain of the welded part when the determined compressive load is applied thereon; and
   evaluating the welding condition of the welded part by judging whether or not the measured amount of strain on measurement is included in a predetermined range.

2. The method for evaluating the welded part as claimed in claim 1, wherein the determined compressive load is applied on a part of the surface of the welded part.

3. The method for evaluating the welded part as claimed in claim 1, wherein the determined compressive load is applied on the welded part through an inspection press member that is adapted so as to press the surface of the welded part.

4. The method for evaluating the welded part as claimed in claim 1, wherein
   there are established, as the welding degrees of the welded parts, a low-strength zone where welded elements forming the welded part are arranged roughly, a high-strength zone where welded elements forming the welded part are arranged closely, and a normal-strength zone where welded elements forming the welded part are arranged with an intermediate density between the low-strength zone and the high-strength zone, and
   the compressive load for inspection is determined within a range of yield loads of the welded parts included in the normal-strength zone.

5. The method for evaluating the welded part as claimed in claim 1, wherein the welded part has a plurality of wires welded with each other.

6. The method for evaluating the welded part as claimed in claim 1, wherein the welded part is formed by means of ultrasonic welding.

7. The method for evaluating the welded part as claimed in claim 3, wherein the inspection press member is provided with a wedge-shaped tip.

8. The method for evaluating the welded part as claimed in claim 3, wherein the inspection press member is provided with a rounded tip.

* * * * *